United States Patent
Bantia et al.

(10) Patent No.: US 6,660,719 B2
(45) Date of Patent: Dec. 9, 2003

(54) INHIBITING T-CELL PROLIFERATION

(75) Inventors: Shanta Bantia, Birmingham, AL (US); John A. Montgomery, Birmingham, AL (US); Philip E. Morris, Jr., Birmingham, AL (US)

(73) Assignee: BioCryst Pharmaceuticals Inc., Birmingham, AL (US)

( * ) Notice: Subject to any disclaimer, the term of this patent is extended or adjusted under 35 U.S.C. 154(b) by 55 days.

(21) Appl. No.: 10/016,108

(22) Filed: Dec. 17, 2001

(65) Prior Publication Data

US 2003/0114466 A1 Jun. 19, 2003

(51) Int. Cl.$^7$ ............................................. A61K 31/70
(52) U.S. Cl. ........................................ 514/43; 514/45
(58) Field of Search ...................... 514/45, 43

(56) References Cited

U.S. PATENT DOCUMENTS 5,985,848 A  * 11/1999  Furneaux et al. ............. 514/44

FOREIGN PATENT DOCUMENTS

WO    WO 01/19375   * 3/2001 ................. 514/45

OTHER PUBLICATIONS

Bantia et al, Purine nucleoside phosphorylase inhibitor BCX–1777 (Immucillin H)—a novel potent and orally active immunosuppresive agent, International Immunopharmacology 1 (2001): 1199–1210.

Kicska et al, Immucillin H, a powerful transition–state analog inhibitor of purine nucleoside phosphorylase, selectively inhibits human t. lymphocytes, PNAS 98 (8), Apr. 10, 2001: 4593–4598.

* cited by examiner

Primary Examiner—Jerome D. Goldberg
(74) Attorney, Agent, or Firm—Connolly Bove Lodge & Hutz LLP

(57) ABSTRACT

T-cell inhibition proliferation in a mammalian host by administering effective amounts of 2'-deoxyguanosine and/or prodrugs thereof; and certain PNP inhibitors.

13 Claims, No Drawings

INHIBITING T-CELL PROLIFERATION

TECHNICAL FIELD

The present invention relates to enhancing the inhibition of T-cell proliferation in a mammalian host and especially a human host. More particularly, the present invention is concerned with enhancing the inhibition of T-cell proliferation by administering 2'-deoxyguanosine and/or prodrugs thereof and certain PNP inhibitors which significantly prolong the half-life of the 2'-deoxyguanosine in a host. The PNP inhibitors employed according to the present invention are disclosed in U.S. Pat. No. 5,985,848 to Schramm et al., entitled "Purine Nucleoside Phosphorylase Inhibitors," disclosure of which is incorporated herein by reference. The process of the present invention enhances the selective inhibition of T-cell proliferation without damaging humoral immunity, which renders the process potentially effective against disorders in which T-cells are pathogenic.

BACKGROUND OF INVENTION

Purine nucleoside phosphorylase (PNP) deficiency is a rare inherited disease accounting for approximately 4% of patients with severe combined immunodeficiency. In PNP deficiency, T- and B-cell immunity are affected. T-cell function may be profoundly deficient, may be normal at birth and then decrease with time, or may fluctuate repeatedly between low and normal. B-cell function can be normal but is deficient in approximately one third of patients. PNP protein is a trimer of approximately 90,000 daltons. It is found in most tissues of the body but is at highest levels in lymphoid tissues. This tissue distribution explains why the lymphoid system is predominantly affected in PNP deficiency. Many mechanisms have been proposed to explain the metabolic toxicity in PNP deficiency. The elevated dGTP found in PNP deficiency is thought to inhibit ribonucleotide reductase and, thus, impede cell division.

8-Aminoguanine given with 2'-deoxyguanosine inhibits the proliferation of human T-cells (CCRF-CEM and Molt-4 cells) in cultures. 8-Aminoguanosine, a soluble derivative which is converted in vivo to 8-aminoguanine, given to rats and dogs with 2'-deoxyguanosine causes a profound fall in peripheral blood lymphocytes and was shown in rats to produce increased levels of 2'-deoxyguanosine triphosphate (dGTP) in T-cells. To produce lymphopenia, inhibition of PNP was required, since 2'-deoxyguanosine alone did not significantly decrease cell counts.

(1S)-1-(9-deazahypoxanthin-9-yl)-1,4-dideoxy-1,4-imino-D-ribitol is one of a family of potent PNP inhibitors. This application provides for administration of exogenous 2'-deoxyguanosine in addition to the PNP inhibitor, which would cause a sufficient accumulation of dGTP exclusively in the T-cells to prevent their proliferation. However, exogenous 2'-deoxyguanosine rapidly degrades upon being administered to a host and therefore is not effective when administered alone. Accordingly, efforts have been underway to discover procedures for significantly prolonging its half-life in a host in order to achieve sufficient accumulation of dGTP in T-cells preventing their proliferation.

SUMMARY OF INVENTION

It has been found according to the present invention that administering certain PNP inhibitors in addition to the exogenous 2'-deoxyguanosine and/or prodrug of 2'-deoxyguanosine results in significantly prolonging the half-life of the 2'-deoxyguanosine. Therefore, the combination of 2'-deoxyguanosine and/or prodrug of 2'-deoxyguanosine and the PNP inhibitors employed according to the present invention provides a potentially effective treatment against disorders in which activated T-cells are pathogenic. For instance, T-cell lymphomas and T-cell leukemias (such as acute lymphoblastic leukemia) maybe treated with a combination of a PNP inhibitor and exogenous 2'-deoxyguanosine and/or prodrug. T-cells have also been implicated in the pathogenesis of autoimmune diseases including rheumatoid arthritis, systemic lupus erythematosus, psoriasis, and type 1 diabetes. This association strongly suggests that the present invention will be an effective therapy for these diseases. Another indication amenable to the treatment described is graft versus host disease (GVHD).

The PNP inhibitors employed according to the present invention are disclosed in U.S. Pat. No. 5,985,848. The PNP inhibitors employed according to the present invention also have a Ki value of about 500 picomolar or less. The PNP inhibitor can be administered along with or prior to the 2'-deoxyguanosine and/or prodrug of 2'-deoxyguanosine.

Still other objects and advantages of the present invention will become readily apparent by those skilled in the art from the following detailed description, wherein it is shown and described only the preferred embodiments of the invention, simply by way of illustration of the best mode contemplated of carrying out the invention. As will be realized the invention is capable of other and different embodiments, and its several details are capable of modifications in various obvious respects, without departing from the invention. Accordingly, the description is to be regarded as illustrative in nature and not as restrictive.

BEST AND VARIOUS MODES FOR CARRYING OUT INVENTION

The present invention relates to enhancing the inhibition of T-cell proliferation in a mammalian host in need of such treatment and especially a human host an effective amount of 2'-deoxyguanosine and/or prodrug of 2'-deoxyguanosine and an effective amount of at least one PNP inhibitor. The PNP inhibitor employed according to the present invention typically has a Ki value of about 500 picomolar or less and preferably about 100 picomolar or less. More particularly, PNP inhibitors employed according to the present invention are disclosed in U.S. Pat. No. 5,985,848 and are represented by the formula (1) shown below.

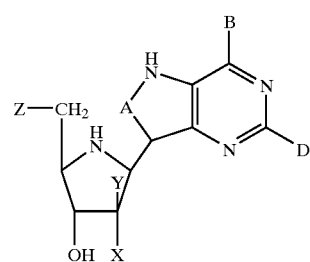

wherein A is CH or N; B is chosen from OH, $NH_2$, NHR, H or halogen; D is chosen from OH, $NH_2$, NHR, H, halogen or $SCH_3$; R is an optionally substituted alkyl, aralkyl or aryl group; and X and Y are independently selected from H, OH or halogen except that when one of X and Y is hydroxy or halogen, the other is hydrogen; and Z is OH or, when X is hydroxy, Z is selected from hydrogen, halogen, hydroxy, SQ or OQ, Q is an optionally substituted alkyl, aralkyl or aryl group; or a tautomer thereof; or a pharmaceutically acceptable salt thereof; or an ester thereof; or a prodrug thereof.

Typically when either of B and/or D is NHR, then R is $C_1$–$C_4$ alkyl.

Typically when one or more halogens are present they are chosen from chlorine and fluorine.

Typically when Z is SQ or OQ, Q is $C_1$–$C_5$ alkyl or phenyl.

Typically D is H, or when D is other than H, B is OH.

More usually B is OH, D is H, OH or $NH_2$, X is OH or H, Y is H, most typically with Z as OH, H or methylthio, especially OH.

It will be appreciated that the representation of a compound of formula (I) wherein B and/or D is a hydroxy group used herein is of the enol-type tautomeric form of a corresponding amide, and this will largely exist in the amide form. The use of the enol-type tautomeric representation is simply to allow fewer structural formulae to represent the compounds of the invention.

Specific suitable PNP inhibitors are:
1. (1S)-1,4-dideoxy-1-C-(4-hydroxypyrrolo[3,2-d]pyrimidin-7-yl)-1,4-imino-D-ribitol
2. (1S)-1-C-(2-amino-4-hydroxypyrrolo[3,2-d]pyrimidin-7-yl)-1,4-dideoxy-1,4-imino-D-ribitol
3. (1R)-1-C-(4-hydroxypyrrolo[3,2-d]pyrimidin-7-yl)-1,4-imino-1,2,4-trideoxy-D-erythro-pentitol
4. (1S)-1-C-(4-hydroxypyrrolo[3,2-d]pyrimidin-7-yl)-1,4-imino-1,4,5-trideoxy-D-ribitol
5. (1S)-1,4-dideoxy-1-C-(4-hydroxypyrrolo[3,2-d]pyrimidin-7-yl)-1,4-imino-5-methylthio-D-ribitol
6. (1S)-1,4-dideoxy-1-C-(2,4-dihydroxypyrrolo[3,2-d]pyrimidin-7-yl)-1,4-imino-D-ribitol
7. (1R)-1-C-(2,4-dihydroxypyrrolo[3,2-d]pyrimidin-7-yl)-1,4-imino-1,2,4-trideoxy-D-erythro-pentitol
8. (1S)-1-C-(2,4-dihydroxypyrrolo[3,2-d]pyrimidin-7-yl)-1,4-imino-1,4,5-trideoxy-D-ribitol
9. (1S)-1,4-dideoxy-1-C-(2,4-dihydroxypyrrolo[3,2-d]pyrimidin-7-yl)-1,4-imino-5-methylthio-D-ribitol
10. (1R)-1-C-(2-amino-4-hydroxypyrrolo[3,2-d]pyrimidin-7-yl)-1,4-imino-1,2,4-trideoxy-D-erythro-pentitol
11. (1S)-1-C-(2-amino-4-hydroxypyrrolo[3,2-d]pyrimidin-7-yl)-1,4-imino-1,4,5-trideoxy-D-ribitol
12. (1S)-1-C-(2-amino-4-hydroxypyrrolo[3,2-d]pyrimidin-7-yl)-1,4-dideoxy-1,4-imino-5-methylthio-D-ribitol
13. (1S)-1,4-dideoxy-1-C-(7-hydroxypyrazolo[4,3-d]pyrimidin-3-yl)-1,4-imino-D-ribitol
14. (1R)-1-C-(7-hydroxypyrazolo[4,3-d]pyrimidin-3-yl)-1,4-imino-1,2,4-trideoxy-D-erythro-pentitol
15. (1S)-1-C-(7-hydroxypyrazolo[4,3-d]pyrimidin-3-yl)-1,4-imino-1,4,5-trideoxy-D-ribitol
16. (1S)-1,4-dideoxy-1-C-(7-hydroxypyrazolo[4,3-d]pyrimidin-3-yl)-1,4-imino-5-methylthio-D-ribitol
17. (1S)-1,4-dideoxy-1-C-(5,7-dihydroxypyrazolo[4,3-d]pyrimidin-3-yl)-1,4-imino-D-ribitol
18. (1R)-1-C-(5,7-dihydroxypyrazolo[4,3-d]pyrimidin-3-yl)-1,4-imino-1,2,4-trideoxy-D-erythro-pentitol
19. (1S)-1-C-(5,7-dihydroxypyrazolo[4,3-d]pyrimidin-3-yl)-1,4-imino-1,4,5-trideoxy-D-ribitol
20. (1S)-1,4-dideoxy-1-C-(5,7-dihydroxypyrazolo[4,3-d]pyrimidin-3-yl)-1,4-imino-5-methylthio-D-ribitol
21. (1S)-1-C-(5-amino-7-hydroxypyrazolo[4,3-d]pyrimidin-3-yl)-1,4-dideoxy-1,4-imino-D-ribitol
22. (1R)-1-C-(5-amino-7-hydroxypyrazolo[4,3-d]pyrimidin-3-yl)-1,4-imino-1,2,4-trideoxy-D-erythro-pentitol
23. (1S)-1-C-(5-amino-7-hydroxypyrazolo[4,3-d]pyrimidin-3-yl)-1,4-imino-1,4,5-trideoxy-D-ribitol
24. (1S)-1-C-(5-amino-7-hydroxypyrazolo[4,3-d]pyrimidin-3-yl)-1,4-dideoxy-1,4-imino-5-methylthio-D-ribitol
25. (1S)-1-C-(3-amino-2-carboxamido-4-pyrrolyl)-1,4-dideoxy-1,4-imino-D-ribitol
26. (1S)-1,4-dideoxy-1-C-(4-hydroxypyrrolo[3,2-d]pyrimidin-7-yl)-1,4-imino-D-ribitol 5-phosphate
27. (1S)-1-C-(2-amino-4-hydroxypyrrolo[3,2-d]pyrimidin-7-yl)-1,4-imino-D-ribitol 5-phosphate
28. (1S)-1-C-(3-amino-2-carboxamido-4-15-pyrrolyl)-1,4-dideoxy-1,4-imino-D-ribitol Preferred are compounds Ib and Ic, their tautomers and pharmaceutically acceptable salts.

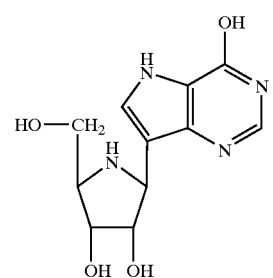

Ib

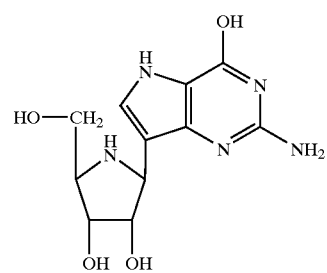

Ic

The most preferred PNP inhibitor employed according to the present invention is (1S)-1-(9-deazahypoxanthin-9-yl)-1,4-dideoxy-1,4-imino-D-ribitol.

Examples of suitable prodrugs of 2'-deoxyguanosine are represented by the following:

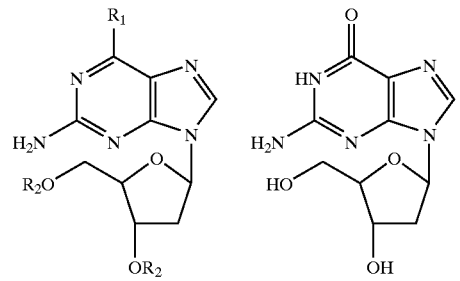

wherein
$R_1$ is $C_1$, $NH_2$, $NHCH_3$, $R_3O$, $R_3S$, or H;
$R_2$ is acyl typically having 1 to 6 carbon atoms, and
$R_3$ is alkyl typically having 1 to 3 carbon atoms and more typically 1 carbon atom.

The first five structural types (i.e.—$R_1$ is $C_1$, $NH_2$, $NHCH_3$, $R_3O$ or $R_3S$) are converted to 2'-deoxyguanosine in vivo by esterases and adenosine deaminase.

The sixth type ($R_1$=H) is oxidized in vivo to 2'-deoxyguanosine. Examples of these in vivo conversions are discussed in Montgomery, *Prog. in Med. Chem.* 7, 69 (1970) and Jones, *Antiviral Chemistry and Chemotherapy* 9, 283 (1998). Mixtures of prodrugs can be employed, if desired, as well as mixtures of one or more prodrugs with 2'-deoxyguanosine.

According to the process of the present invention, the PNP inhibitor is administered prior to or at the same time as the 2'-deoxyguanosine and/or prodrug of 2'-deoxyguanosine. The PNP should be present in the host's bloodstream with 2'-deoxyguanosine in order to effectively prolong the half-life of the 2'-deoxyguanosine to permit a sufficient accumulation of 2'-deoxyguanosine triphosphate in T-cells to prevent their proliferation. When the PNP inhibitor is administered prior to the 2'-deoxyguanosine and/or prodrug of 2'-deoxyguanosine it is typically administered up to about 1 hour prior to the 2'-deoxyguanosine and/or prodrug of 2'-deoxyguanosine.

The compounds of the present invention can be administered by any conventional means available for use in conjunction with pharmaceuticals, either as individual therapeutic agents or in a combination of therapeutic agents. They can be administered alone, but generally administered with a pharmaceutical carrier selected on the basis of the chosen route of administration and standard pharmaceutical practice.

The dosage administered will, of course, vary depending upon known factors, such as the pharmacodynamic characteristics of the particular agent and its mode and route of administration; the age, health and weight of the recipient; the nature and extent of the symptoms, the kind of concurrent treatment; the frequency of treatment; and the effect desired. A daily dosage of active ingredient can be expected to be about 0.001 to 1000 milligram (mg) per kilogram (kg) of body weight, with the preferred dose being 0.1 to about 30 mg/kg.

Dosage forms (compositions suitable for administration) contain from about 1 mg to about 100 mg of active ingredient per unit. In these pharmaceutical compositions, the active ingredient will ordinarily be present in an amount of about 0.5–95% by weight based on the total weight of the composition.

The active ingredient can be administered orally in solid dosage forms, such as capsules, tablets, and powders, or in liquid dosage forms, such as elixirs, syrups, and suspensions. It can also be administered parenterally, in sterile liquid dosage forms. The active ingredient can also be administered intranasally (nose drops) or by inhalation. Other dosage forms are potentially possible such as administration transdermally, via a patch mechanism or ointment.

Gelatin capsules contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar-coated or film-coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water-soluble salt of the active ingredient, suitable stabilizing agents, and, if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propylparaben, and chlorobutanol.

Suitable pharmaceutical carriers are described in Remington's Pharmaceutical Sciences, Mack Publishing Company, a standard reference text in this field.

Useful pharmaceutical dosage forms for administration of the compounds according to the present invention can be illustrated as follows:

Capsules

A large number of unit capsules are prepared by filling standard two-piece hard gelatin capsules each with 100 mg of powdered active ingredient, 150 mg of lactose, 50 mg of cellulose, and 6 mg of magnesium stearate.

Soft Gelatin Capsules

A mixture of active ingredient in a digestible oil such as soybean oil, cottonseed oil, or olive oil is prepared and injected by means of a positive displacement pump into gelatin to form soft gelatin capsules containing 100 mu of the active ingredient. The capsules are washed and dried.

Tablets

A large number of tablets are prepared by conventional procedures so that the dosage unit was 100 mg of active ingredient, 0.2 mg of colloidal silicon dioxide, 5 mg of magnesium stearate, 275 mg of microcrystalline cellulose, 11 mg of starch, and 98.8 mg of lactose. Appropriate coatings may be applied to increase palatability or delay absorption.

Moreover, the compounds of the present invention can be administered in the form of nose drops or a nasal inhaler.

Various modifications of the invention in addition to those shown and described herein will be apparent to those skilled in the art from the foregoing description. Such modifications are also intended to fall within the scope of the appended claims.

The foregoing disclosure includes all the information deemed essential to enable those skilled in the art to practice the claimed invention. Because the cited applications may provide further useful information, these cited materials are hereby incorporated by reference in their entirety.

The foregoing description of the invention illustrates and describes the present invention. Additionally, the disclosure shows and describes only the preferred embodiments of the invention but, as mentioned above, it is to be understood that the invention is capable of use in various other combinations, modifications, and environments and is capable of changes or modifications within the scope of the inventive concept as expressed herein, commensurate with the above teachings and/or the skill or knowledge of the relevant art. The embodiments described hereinabove are further intended to explain best modes known of practicing the invention and to enable others skilled in the art to utilize the invention in such, or other, embodiments and with the various modifications required by the particular applications or uses of the invention. Accordingly, the description is not intended to limit the invention to the form disclosed herein. Also, it is intended that the appended claims be construed to include alternative embodiments.

What is claimed is:

1. A process for enhancing the inhibition of T-cell proliferation in a mammalian host in need thereof by administering to said boat an enhanced effective amount of 2'-deoxyguanosine, and at least one PNP inhibitor having a Ki of 500 picomolar or less and wherein said at least one PNP inhibitor comprises at least one compound represented by the formula:

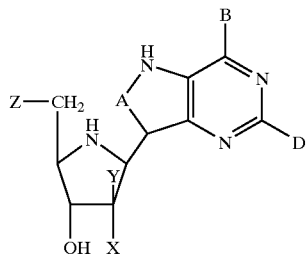

wherein A is CH or N; B is selected from the group consisting of OH, NH₂, NHR, H or halogen; D is selected from the group consisting of OH, NH₂, NHR, H, halogen or SCH₃; R is an optionally substituted alkyl, aralkyl or aryl group; and X and Y are independently selected from the group consisting of H, OH or halogen except that when one of X and Y is hydroxy or halogen, the other is hydrogen; and Z is OH or, when X is hydroxy, Z is selected from hydrogen, halogen, hydroxy, SQ or OQ, Q is an optionally substituted alkyl, aralkyl or aryl group; or a tautomer thereof; or a pharmaceutically acceptable salt thereof; or an ester thereof.

2. The process of claim 1 wherein the PNP inhibitor is administered simultaneously with the 2'-deoxyguanosine or prior to the 2'-deoxyguanosine.

3. The process of claim 1 wherein the PNP inhibitor is administered up to about 1 hour prior to administering the 2'-deoxyguanosine.

4. The process of claim 1 which comprises orally administering the inhibitor.

5. The process of claim 4 which comprises administering the 2'-deoxyguanosine by infusion.

6. The process of claim 4 which comprises orally administering the at least one member.

7. The process of claim 1 wherein the PNP inhibitor comprises at least one member selected from the group consisting of (1S)-1,4-dideoxy-1-C-(4-hydroxypyrrolo[3,2-d]pyrimidin-7-yl)-1,4-imino-D-ribitol; (1S)-1-C-(2-amino-4-hydroxypyrrolo[3,2-d]pyrimidin-7-yl)-1,4-dideoxy-1,4-imino-D-ribitol; (1R)-1-C-(4-hydroxypyrrolo[3,2-d]pyrimidin-7-yl)-1,4-imino-1,2,4-trideoxy-D-erythro-pentitol; (1S)-1-C-(4-hydroxypyrrolo[3,2-d]pyrimidin-7-yl)-1,4-imino-1,4,5-trideoxy-D-ribitol; (1S)-1,4-dideoxy-1-C-(4-hydroxypyrrolo[3,2-d]pyrimidin-7-yl)-1,4-imino-5-methylthio-D-ribitol; (1S)-1,4-dideoxy-1-C-(2,4-dihydroxypyrrolo[3,2-d]pyrimidin-7-yl)-1,4-imino-D-ribitol; (1R)-1-C-(2,4-dihydroxypyrrolo[3,2-d]pyrimidin-7-yl)-1,4-imino-1,2,4-trideoxy-D-erythro-pentitol; (1S)-1-C-(2,4-dihydroxypyrrolo[3,2-d]pyrimidin-7-yl)-1,4-imino-1,4,5-trideoxy-D-ribitol; (1 S)-1,4-dideoxy-1-C-(2,4-dihydroxypyrrolo[3,2-d]pyrimidin-7-yl)-1,4-imino-5-methylthio-D-ribitol; (1R)-1-C-(2-amino-4-hydroxypyrrolo[3,2-d]pyrimidin-7-yl)-1,4-imino-1,2,4-trideoxy-D-erythro-pentitol; (1S)-1-C-(2-amino-4-hydroxypyrrolo [3,2-d]pyrimidin-7-yl)-1,4-imino-1,4,5-trideoxy-D-ribitol; (1S)-1-C-(2-amino-4-hydroxypyrrolo [3,2-d]pyrimidin-7-yl)-1,4-dideoxy-1,4-imino-5-methylthio-D-ribitol; (1S)-1,4-dideoxy-1-C-(7-hydroxypyrazolo [4,3-d]pyrimidin-3-yl)-1,4-imino-D-ribitol; (1R)-1-C-(7-hydroxypyrazolo [4,3-d]pyrimidin-3-yl)-1,4-imino-1,2,4-trideoxy-D-erythro-pentitol; (1S)-1-C-(7-hydroxypyrazolo [4,3-d]pyrimidin-3-yl)-1,4-imino-1,4,5-trideoxy-D-ribitol; (1S)-1,4-dideoxy-1-C-(7-hydroxypyrazolo [4,3-d]pyrimidin-3-yl)-1,4-imino-5-methylthio-D-ribitol; (1S)-1,4-dideoxy-1-C-(5,7-dihydroxypyrazolo[4,3-d]pyrimidin-3-yl)-1,4-imino-D-ribitol; (1R)-1-C-(5,7-dihydroxypyrazolo[4,3-d]pyrimidin-3-yl)-1,4-imino-1,2,4-trideoxy-D-erythro-pentitol; (1S)-1-C-5,7-dihydroxypyrazolo[4,3-d]pyrimidin-3-yl)-1,4-imino-1,4,5-trideoxy-D-ribitol; (1S)-1,4-dideoxy-1-C-(5,7-dihydroxypyrazolo[4,3-d]pyrimidin-3-yl)-1,4-imino-5-methylthio-D-ribitol; (1S)-1-C-(5-amino-7-hydroxypyrazolo[4,3-d]pyrimidin-3-yl)-1,4-dideoxy-1,4-imino-D-ribitol; (1R)-1-C-(5-amino-7-hydroxypyrazolo[4,3-d]pyrimidin-3-yl)-1,4-imino-1,2,4-trideoxy-D-erytliro-pentitol; (1S)-1-C-(5-amino-7-hydroxypyrazolo [4,3-d]pyrimidin-3-yl)-1,4-imino-1,4,5-trideoxy-D-ribitol; (1S)-1-C-(5-amino-7-hydroxypyrazolo[4,3-d]pyrimidin-3-yl)-1,4-dideoxy-1,4-imino-5-methylthio-D-ribitol; (1S)-1-C-(3-amino-2-carboxamido-4-pyrrolyl)-1,4-dideoxy-1,4-imino-D-ribitol; (1S)-1,4-dideoxy-1-C-(4-hydroxypyrrolo[3,2-d]pyrimidin-7-yl)-1,4-imino-D-ribitol 5-phosphate; (1S)-1-C-(2-amino-4-hydroxypyrrolo [3,2-d]pyrimidin-7-yl)-1,4-imino-D-ribitol 5-phosphate; and (1S)-1-C-(3-amino-2-carboxamido-4-15-pyrrolyl)-1,4-dideoxy-1,4-imino-D-ribitol; or a tautomer thereof; or a pharmaceutically acceptable salt thereof; or an ester thereof; or a prodrug thereof.

8. The process of claim 1 wherein the PNP inhibitor comprises at least one member represented by the formulae:

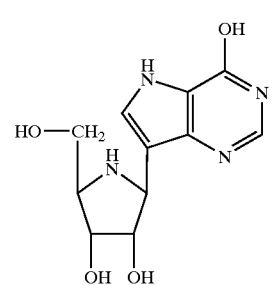

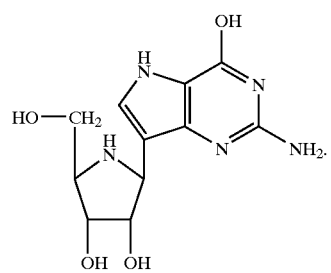

9. A process for enhancing the inhibition of T-cell proliferation in a mammalian host in need thereof by orally administering to said host an enhanced effective amount of 2'-deoxyguanosine and administering to said bust an effective amount of (1S)-1-(9-deazahypoxanthin-9-yl)-1,4-dideoxy-1,4-imino-D-ribitol; and wherein the T-cell proliferation is sensitive to the above combination.

10. The process of claim 9 wherein the PNP inhibitor is administered simultaneously with the 2'-deoxyguanosine or prior to the 2'-deoxyguanosine.

11. The process of claim 9 wherein the PNP inhibitor is administered up to about 1 hour prior to administering the 2'-deoxyguanosine.

12. The process of claim 9 which comprises orally administering the inhibitor.

13. The process of claim 9 which comprises administering the 2'-deoxyguanosine by infusion.

* * * * *